US007294650B2

(12) United States Patent
Biggadike

(10) Patent No.: US 7,294,650 B2
(45) Date of Patent: Nov. 13, 2007

(54) BENZOTHIOPHEN AND THIOCHRONE CONTAINING PHENETHANOLAMINE DERIVATIVES FOR THE TREATMENT OF RESPIRATORY DISORDERS

(75) Inventor: Keith Biggadike, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/595,997

(22) PCT Filed: Dec. 15, 2004

(86) PCT No.: PCT/EP2004/014381

§ 371 (c)(1),
(2), (4) Date: May 24, 2006

(87) PCT Pub. No.: WO2005/058867

PCT Pub. Date: Jun. 30, 2005

(65) Prior Publication Data

US 2007/0172385 A1    Jul. 26, 2007

(30) Foreign Application Priority Data

Dec. 17, 2003 (GB) ................... 0329182.0

(51) Int. Cl.
*A61K 31/535* (2006.01)
*A61K 31/47* (2006.01)
*A61K 31/44* (2006.01)
*A61K 31/42* (2006.01)
*A61K 31/38* (2006.01)

(52) U.S. Cl. ............. 514/432; 514/229.2; 514/230.5; 514/312; 514/333; 514/375; 514/378; 544/2; 544/105; 546/153; 546/158; 546/280.1; 548/159; 548/247; 548/527; 549/23

(58) Field of Classification Search ............. 514/229.2, 514/230.5, 312, 333, 375, 378, 432; 544/2, 544/105; 546/153, 158, 280.1; 548/159, 548/247, 527; 549/23

See application file for complete search history.

(56) References Cited

U.S. PATENT DOCUMENTS

| 2,918,408 | A | 12/1959 | Biel |
| 4,353,365 | A | 10/1982 | Hallworth et al. |
| 4,778,054 | A | 10/1988 | Newell et al. |
| 4,811,731 | A | 3/1989 | Newell et al. |
| 4,992,474 | A | 2/1991 | Skidmore et al. |
| 5,035,237 | A | 7/1991 | Newell et al. |
| 5,590,645 | A | 1/1997 | Davies et al. |
| 5,860,419 | A | 1/1999 | Davies et al. |
| 5,873,360 | A | 2/1999 | Davies et al. |
| 6,321,747 | B1 | 11/2001 | Dmitrovic et al. |
| 6,632,666 | B2 | 10/2003 | Baust et al. |

FOREIGN PATENT DOCUMENTS

| DE | 3524990 | 1/1986 |
| EP | 69715 | 1/1983 |
| EP | 162576 | 11/1985 |
| EP | 220054 | 4/1987 |
| EP | 0303465 | 2/1989 |
| EP | 0947498 | 10/1999 |
| GB | 2064336 | 6/1981 |
| GB | 2129691 | 5/1984 |
| GB | 2165542 | 4/1986 |
| GB | 2169265 | 7/1986 |
| GB | 2178965 | 2/1987 |
| GB | 2230523 | 10/1990 |
| GB | 2242134 | 9/1991 |
| WO | WO99/16766 | 4/1999 |
| WO | WO99/47505 | 9/1999 |
| WO | WO 01/04118 | 1/2001 |
| WO | WO 01/13953 | 3/2001 |
| WO | WO 02/066422 | 8/2002 |
| WO | WO 03/024439 | 3/2003 |

OTHER PUBLICATIONS

Fujii et al., "Novel phosphodiesterase 4 inhibitor T-440 reverses and prevents human bronchial contraction induced by allergen," *J Pharmacol Exp Ther* 284(1):162 (1998).

Landells et al., "Oral administration of the phosphodiesterase (PDE)4 inhibitor, V11294A inhibits ex-vivo agonist-induced-cell activation," *Eur Resp J* (/annu Cong Eur Resp Soc, Geneva) 12(Suppl. 28) Abst P2393 (Sep. 1998).

Apperley et al., "Selectivity of Beta-adrenoceptor agonists and antagonists on bronchial, skeletal, vascular and cardiac muscle in the anaesthetized cat," *British Journal of Pharmacology* 57(2):235-246 (1976).

Primary Examiner—Peter O'Sullivan
(74) Attorney, Agent, or Firm—Robert J. Smith

(57) ABSTRACT

Compounds of formula (I):

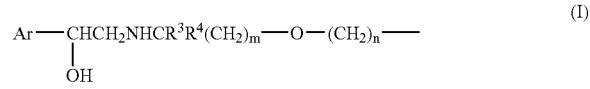

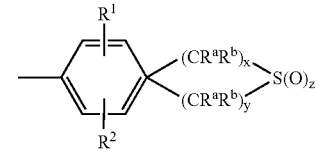

and salts, solvates, and physiologically functional derivatives thereof, useful for the prophylaxis or treatment of a clinical condition for which a selective $\beta_2$-adrenoreceptor agonist is indicated, for example asthma or chronic obstructive pulmonary disease (COPD).

19 Claims, No Drawings

BENZOTHIOPHEN AND THIOCHRONE CONTAINING PHENETHANOLAMINE DERIVATIVES FOR THE TREATMENT OF RESPIRATORY DISORDERS

CROSS-REFERENCE TO RELATED APPLICATIONS

This application is filed pursuant to 35 U.S.C. § 317 as a U.S. National Phase Application of International Application No. PCT/EP2004/014381 filed Dec. 15, 2004, which claims priority from GB0329182.0 filed Dec. 17, 2003.

FIELD OF THE INVENTION

The present invention is concerned with phenethanolamine derivatives, processes for their preparation, compositions containing them and their use in medicine, particularly in the prophylaxis and treatment of respiratory diseases.

BACKGROUND OF THE INVENTION

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the duration of action is approximately 12 hours, hence twice daily dosing is often required. There is therefore a clinical need for compounds having potent and selective stimulant action at $\beta_2$-adrenoreceptors and having an advantageous profile of action.

SUMMARY OF THE INVENTION

According to the present invention, there is provided a compound of formula (I)

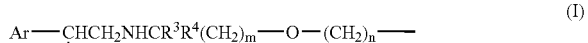

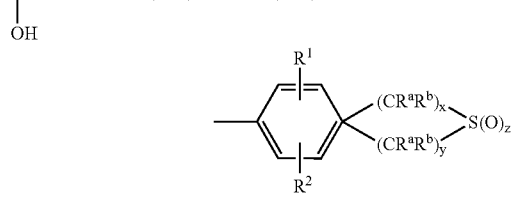

or a salt, solvate, or physiologically functional derivative thereof, wherein:
m is an integer of from 2 to 8;
n is an integer of from 3 to 11, preferably from 3 to 7;
with the proviso that m+n is 5 to 19, preferably 5 to 12;
x is zero and y is an integer of 2 or 3 or
y is zero and x is an integer of 2 or 3;
z is zero or an integer of 1 or 2;
$R^a$ and $R^b$ are independently selected from hydrogen and $C_{1-4}$alkyl;

$R^1$ and $R^2$ are independently selected from hydrogen, $C_{1-6}$alkyl, $C_{1-6}$alkoxy, halo, phenyl, and $C_{1-6}$haloalkyl;
$R^3$ and $R^4$ are independently selected from hydrogen and $C_{1-4}$alkyl with the proviso that the total number of carbon atoms in $R^3$ and $R^4$ is not more than 4;
Ar is a group selected from

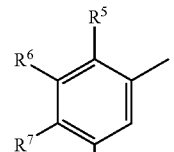

(a)

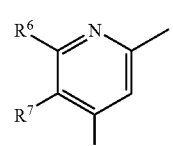

(b)

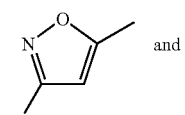

(c)

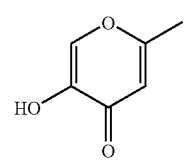

(d)

wherein $R^6$ represents hydrogen, halogen, —$(CH_2)_qOR^9$, —$NR^9C(O)R^{10}$, —$NR^9SO_2R^{10}$, —$SO_2NR^9R^{10}$, —$NR^9R^{10}$, —$OC(O)R^{11}$ or —$OC(O)NR^9R^{10}$,
and $R^5$ represents hydrogen, halogen or $C_{1-4}$alkyl;
or $R^6$ represents —$NHR^{12}$ and $R^5$ and —$NHR^{12}$ together form a 5- or 6- membered heterocyclic ring;
$R^7$ represents hydrogen, halogen, —$OR^9$ or —$NR^9R^{10}$;
$R^8$ represents hydrogen, halogen, halo$C_{1-4}$ alkyl, —$OR^9$, —$NR^9R^{10}$, —$OC(O)R^{11}$ or —$OC(O)NR^9R^{10}$;
$R^9$ and $R^{10}$ independently represent hydrogen or $C_{1-4}$ alkyl or $R^9$ and $R^{10}$ together with the nitrogen atom to which they are attached form a 5-, 6- or 7- membered nitrogen-containing ring,
$R^{11}$ represents an aryl (eg phenyl or naphthyl) group which may be unsubstituted or substituted by one or more substituents selected from halogen, $C_{1-4}$ alkyl, hydroxy, $C_{1-4}$ alkoxy or halo $C_{1-4}$ alkyl; and
q is zero or an integer from 1 to 4.

In the compounds of formula (I), $R^3$ and $R^4$ are preferably independently selected from hydrogen and methyl, more preferably $R^3$ and $R^4$ are both hydrogen.

In the compounds of formula (I) $R^1$ and $R^2$ preferably each represent hydrogen.

m is suitably 4, 5 or 6 and n is suitably 3, 4, 5 or 6. Preferably m is 5 or 6 and n is 3 or 4, such that m+n is 8, 9 or 10, preferably 9.

Z preferably represents 2.

In the compounds of formula (I) the group Ar is preferably selected from groups (a) and (b) above.

In said groups (a) and (b) when $R^6$ represents halogen this is preferably chlorine or fluorine.

$R^9$ and $R^{10}$ preferably each independently represent hydrogen or methyl.

$R^{11}$ preferably represents substituted phenyl.

The integer q preferably represents zero or 1.

Thus for example:

—$(CH_2)_qOR^9$ preferably represents —OH or —$CH_2OH$,

—$NR^9C(O)R^{10}$ preferably represents —NHC(O)H, $SO_2NR^9R^{10}$ preferably represents —$SO_2NH_2$ or —$SO_2NHCH_3$, —$NR^9R^{10}$ preferably represents —$NH_2$, —$OC(O)R^{11}$ preferably represents substituted benzoyloxy eg. —$OC(O)C_6H_4$-($p$-$CH_3$); and —$OC(O)NR^9R^{10}$ preferably represents —$OC(O)N(CH_3)_2$.

When $R^6$ represents $NHR^{12}$ and together with $R^5$ forms a 5- or 6- membered heterocyclic ring —$NHR^{12}$—$R^5$- preferably represents a group:

—NH—CO—$R^{13}$ where $R^{13}$ is an alkyl, alkenyl or alkyloxy group;

—NH—$SO_2R^{14}$ where $R^{14}$ is an alkyloxy group;

—NH—$R^{15}$ where $R^{15}$ is an alkyl or alkenyl group optionally substituted by ($COOR^{16}$) and where $R^{16}$ is $C_{1-4}$ alkyl; or —NH—CO—S;

wherein said alkyl, and alkenyl groups and moieties contain 1 or 2 carbon atoms.

Particularly preferred groups (a) and (b) may be selected from the following groups (i) to (xxi):

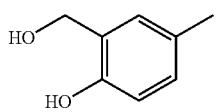
(i)

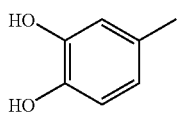
(ii)

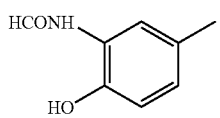
(iii)

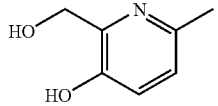
(iv)

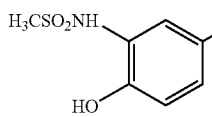
(v)

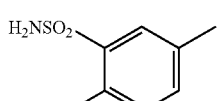
(vi)

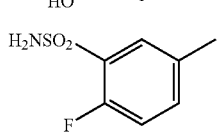
(vii)

-continued

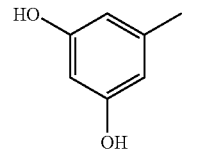
(viii)

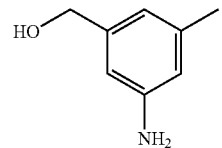
(ix)

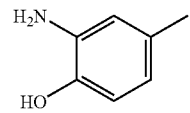
(x)

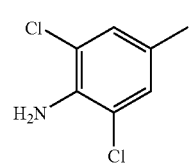
(xi)

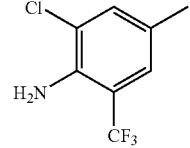
(xii)

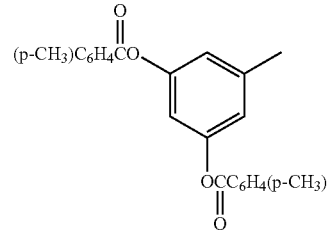
(xiii)

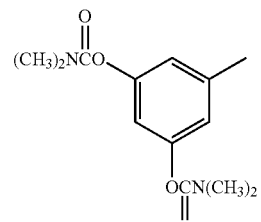
(xiv)

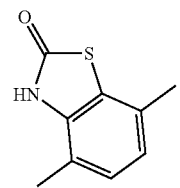
(xv)

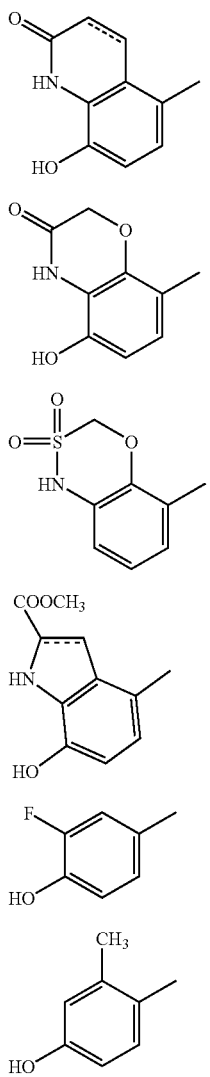

wherein the dotted line in (xvi) and (xix) denotes an optional double bond.

Preferably Ar represents a group (i).

It is to be understood that the present invention covers all combinations of particular and preferred groups described hereinabove.

DETAILED DESCRIPTION

It will be appreciated that the compounds of formula (I) and (Ia) include an asymmetric centre, namely the carbon atom of the

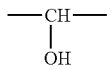

group. The compounds may therefore exist in two different isomeric forms in respect of said chiral centre. The present invention includes both (S) and (R) enantiomers at said chiral centre either in substantially pure form or admixed in any proportions. Similarly, where $R^3$ and $R^4$ are different groups or where $R^a$ and $R^b$ are different groups, the carbon atom to which they are attached is an asymmetric centre and the present invention includes both (S) and (R) enantiomers at this centre either in substantially pure form or admixed in any proportions. In addition, when z represents 1 an asymmetric centre exists at the sulfur atom of the sulfoxide moiety.

Thus the compounds of formula (I) include all enantiomers (including the sulfoxide (S) and (R) enantiomers) and diastereoisomers as well as mixtures thereof in any proportions.

Salts and solvates of compounds of formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable salts, solvates, and physiologically functional derivatives.

By the term "physiologically functional derivative" is meant a chemical derivative of a compound of formula (I) having the same physiological function as the parent compound of formula (I) for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, m-toluenesulphonic, benzenesulphonic, 4-chlorobenzenesulphonic, 4-bromobenzenesulphonic, 4-phenylbenzenesulphonic, naphthalenesulphonic or naphthalenedisulphonic), salicylic, glutaric, gluconic, tricarballylic, cinnamic, substituted cinnamic (for example, phenyl, methyl, cynao, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters of the compounds of formula (I) and (Ia) may have a hydroxyl group converted to a $C_{1-6}$alkyl, aryl, aryl $C_{1-6}$ alkyl, or amino acid ester.

As mentioned above, the compounds of formula (I) are selective $\beta_2$-adrenoreceptor agonists as demonstrated using functional or reporter gene readout from cell lines transfected with human beta-adrenoreceptors, or membranes derived from these cells, as described below. Compounds according to the present invention also have the potential to combine long duration of effect with rapid onset of action.

Compounds of formula (I) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I) or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I) or a pharmaceutically acceptable salt, solvate, or physiologically functional derivative thereof for use in medical therapy, particularly, for use in the prophylaxis or treatment of a clinical condition in a mammal, such as a human, for which a selective $P_2$-adrenoreceptor agonist is indicated. In particular, there is provided a compound of formula (I) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I) or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I) or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I) or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. eg. 0.05 mg to 0.5 mg. The dose range for adult humans is generally from 0.0005 mg to 10 mg per day and preferably 0.01 mg to 1 mg per day, most preferably 0.05 mg to 0.5 mg.

While it is possible for the compound of formula (I) or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I) or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (eg. lactose or starch). Use of lactose is preferred.

Each capsule or cartridge may generally contain between 20 μg-10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (eg as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,365, the disclosures of which are hereby incorporated by reference). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β1-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1, 4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 3 Sep., 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD12-281 from elbion (Hofgen, N. et al. 15th EFMC Int Symp Med Chem (Sept 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer, a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sept 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methyl-benzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther,1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data:

Atropine—CAS-51-55-8 or CAS-51-48-1 (anhydrous form), atropine sulfate —CAS-5908-99-6; atropine oxide —CAS-4438-22-6 or its HCl salt —CAS-4574-60-1 and methylatropine nitrate—CAS-52-88-0.

Homatropine —CAS-87-00-3, hydrobromide salt —CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt-CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

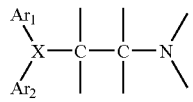

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperazine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) or a pharmaceutically acceptable salt, solvate or physiologically functional derivative thereof together with a PDE4 inhibitor.

The invention thus provides, in a further aspect, a combination comprising a compound of formula (I) or (Ia) or a pharmaceutically acceptable salt, solvate or physiologically functional derivative thereof together with a corticosteroid. Preferably, the invention provides a combination comprising a compound of formula (Ia) or a pharmaceutically acceptable salt, solvate or physiologically functional derivative thereof together with a preferred corticosteroid as described hereinabove, e.g. fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

The invention thus provides, in a further aspect, a combination comprising a compound of formula (I) or a pharmaceutically acceptable salt, solvate or physiologically functional derivative thereof together with an anticholinergic.

The invention thus provides, in a further aspect, a combination comprising a compound of formula (I) or a pharmaceutically acceptable salt, solvate or physiologically functional derivative thereof together with an antihistamine.

The invention thus provides, in a further aspect, a combination comprising a compound of formula (I) or a pharmaceutically acceptable salt, solvate or physiologically functional derivative thereof together with a PDE4 inhibitor and a corticosteroid.

The invention thus provides, in a further aspect, a combination comprising a compound of formula (I) or a pharmaceutically acceptable salt, solvate or physiologically functional derivative thereof together with an anticholinergic and a PDE4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I) or a salt, solvate, or physiologically functional derivative thereof which comprises a process as defined below followed by the following steps in any order:
(i) optional removal of any protecting groups;
(ii) optional separation of an enantiomer from a mixture of enantiomers;
(iii) optional conversion of one compound of formula (I) to a different compound of formula (I)
(iv) optional conversion of the product to a corresponding salt, solvate, or physiologically functional derivative thereof.

In one general process (a), a compound of formula (I) may be obtained by deprotection of a protected intermediate, for example of formula (II):

$$Ar^1-\underset{OP^1}{CHCH_2}NP^2CR^3R^4(CH_2)_m-O-(CH_2)_n-\text{Ar}-S(O)_z \quad (II)$$

or a salt or solvate thereof, wherein $R^a$, $R^b$, $R^1$, $R^2$, $R^3$, $R^4$, m, n, x, y and z are as defined for the compound of formula (I) or (Ia), $Ar^1$ represents an optionally protected form of Ar; and $P^1$ and $P^2$ are each independently either hydrogen or a protecting group, such that the compound of formula (II) contains at least one protecting group.

Optionally protected forms of the preferred groups Ar may be selected from:

(ia), (iia), (iiia), (iva), (va), (via), (viia), (viiia), (ixa), (xa), (xia), (xiia)

-continued

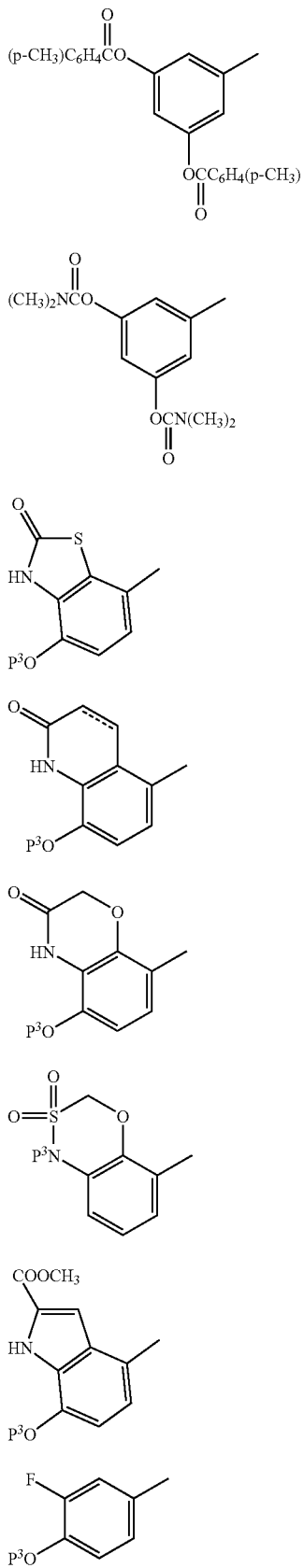

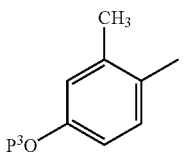

(xxia)

wherein P³ and P⁴ are each independently either hydrogen or a protecting group, and the dotted line in (xvia) and (xixa) denotes an optional double bond. It will be appreciated that when Ar¹ is a group (viia) or any one of (xia) to (xiva) no protection is required, and hence in these instances Ar¹ is equivalent to Ar.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by P³ and P⁴ are esters such as acetate ester, aralkyl groups such as benzyl, diphenylmethyl, or triphenylmethyl, and tetrahydropyranyl. Examples of suitable amino protecting groups represented by P² include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CHOP¹ using, for example, a trialkylsilyl group such as triethylsilyl. A person skilled in the art will also appreciate other orthogonal protection strategies, available by conventional means as described in Theodora W Greene (see above).

The deprotection to yield a compound of formula (I) or (Ia) may be effected using conventional techniques. Thus, for example, when P², P³, and/or P⁴ is an aralkyl group, this may be cleaved by hydrogenolysis in the presence of a metal catalyst (e.g. palladium on charcoal).

When P³ and/or P⁴ is tetrahydropyranyl this may be cleaved by hydrolysis under acidic conditions. Acyl groups represented by P² may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above).

In a particular embodiment of process (a), when Ar represents a group of structure (i), eg. as in formula (Ia), P³ and P⁴ may together represent a protecting group as in the compound of formula (III).

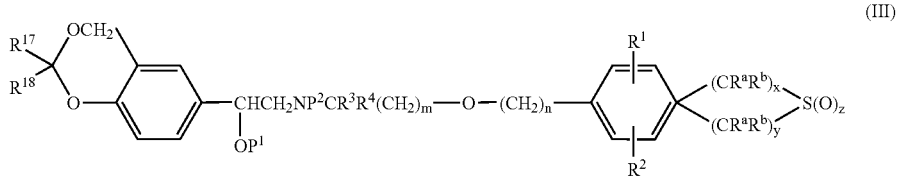
(III)

or a salt or solvate thereof, wherein $R^a$, $R^b$, $R^1$, $R^2$, $R^3$, $R^4$, $R^5$, $P^1$, $P^2$, m, n, x, y and z are as defined for the compound of formula (I) $R^{17}$ and $R^{18}$ are independently selected from hydrogen, $C_{1-6}$alkyl, or aryl or $R^{17}$ and $R^{18}$ together form a $C_{3-7}$alkyl group. In a preferred aspect, both $R^{17}$ and $R^{18}$ are methyl.

A compound of formula (III) may be converted to a compound of formula (I) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

It will be appreciated that the protecting groups $P^1$, $P^2$, $P^3$ and $P^4$ (including the cyclised protecting group formed by $P^3$ and $P^4$ as depicted in formula (III) may be removed in a single step or sequentially. The precise order in which protecting groups are removed will in part depend upon the nature of said groups and will be readily apparent to the skilled worker. Preferably, when $P^3$ and $P^4$ together form a protecting group as in formula (III) this protecting group is removed together with any protecting group $P^1$ on the CH(OH) moiety, followed by removal of $P^2$.

Compounds of formula (II) and (III) may be prepared by reaction of a compound of formula (IV):

(IV)

wherein $Ar^1$ is as defined above for formula (II) and $P^1$ and $P^2$, each independently represent hydrogen or a protecting group, with a compound of formula (V):

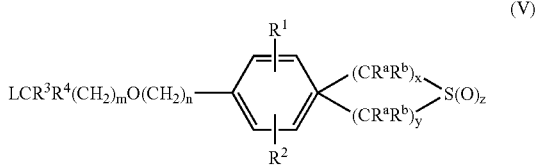
(V)

wherein L is a leaving group such as halo (typically, bromo or iodo) or a sulfonate such as an alkylsulfonate (typically methanesulfonate), an aryl sulfonate (typically toluenesulfonate) or a haloalkylsulfonate, (typically trifluoromethanesulfonate) and $R^a$, $R^b$, $R^1$, $R^2$, $R^3$, $R^4$, n, m, x, y and z are as defined for compounds of formula (I).

The reaction of compounds of formula (IV) and (V) is optionally effected in the presence of an organic base, such as a trialkylamine, for example diisopropylethylamine, and in a suitable solvent, for example dimethylformanide.

It will be appreciated that when a compound of formula (IV) is employed wherein each of $P^1$ and $P^2$ together with any groups $P^3$ and $P^4$ in $Ar^1$, represents hydrogen, the reaction of compounds (IV) and (V) will directly form a compound of formula (I).

Therefore in a further aspect the present invention provides a further process (b) which comprises reaction of a compound of formula (IV) wherein each of $P^1$, $P^2$, $P^3$ and $P^4$ represent hydrogen, with a compound of formula (V).

Compounds of formula (IV) are known in the art or may be prepared by methods well known in the art.

Thus, for example, details concerning preparation of compounds (IV) wherein $Ar^1$ is a group (ia) may be found in EP-A-0947498; concerning preparation of compounds (IV) wherein $Ar^1$ is a group (va) in DE3524990; concerning the preparation of compounds (IV) wherein $Ar^1$ is a group (iia), (viia), and (xvia) in EP-A-162576; concerning the preparation of compounds (IV) wherein $Ar^1$ is a group (iva) in EP-A-220054; concerning the preparation of compounds (IV) wherein $Ar^1$ is a group (xia) in GB2165542 and concerning the preparation of compounds (IV) wherein $Ar^1$ is a group (c) in GB2230523.

A compound of formula (V) may be prepared by reacting an olefin of formula (VI):

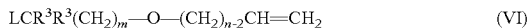
(VI)

wherein L, $R^3$, $R^4$, m and n are as defined for formula (V), with a compound of formula (VII):

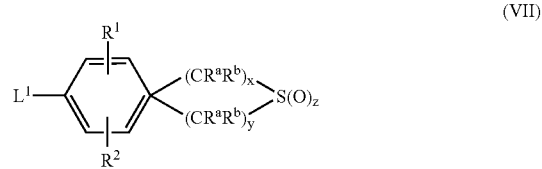
(VII)

wherein $L^1$ is a leaving group as defined for formula (V) and $R^a$, $R^b$, $R^1$, $R^2$, x, y and z are as defined for formula (V).

In this method, a compound of formula (VI) is initially reacted with a sterically hindered borane compound eg. a cyclic borane derivative such as 9-borabicyclo[3.3.1] nonane, thexylborane, catecholborane or disiamylborane, and followed by coupling with the compound (VII) in the presence of a catalyst such as palladium acetate, $PdCl_2$, $Pd(PPh_3)_4$, or $Pd_2(dba)_3$; and a phosphine such as triphenylphosphine, (di-tert-butylphosphino)biphenyl, tricyclohexylphosphine, triisopropylphosphine, tricyclopentylphosphine, or tri-tert-butylphosphine; and a base such as aqueous potassium or sodium phosphate, potassium, cesium or sodium carbonate, or sodium acetate. The reaction may conveniently be effected in a suitable solvent such as tetrahydrofuran.

Compounds of formula (VI) may be prepared by standard methods well known to those skilled in the art, for example from the corresponding dihaloalkane and hydroxyalkene, by conventional chemistry, typically in the presence of an inorganic base, such as aqueous sodium hydroxide, under phase transfer conditions in the presence of an ammonium salt such as tetraalkylammonium bromide.

Compounds of formula (VII) may be prepared by standard methods from commercially available precursors.

Compounds of formulae (II) and (III) wherein $P^1$ and $P^2$ are hydrogen may alternatively be prepared from the corresponding compound of formula (VIII).

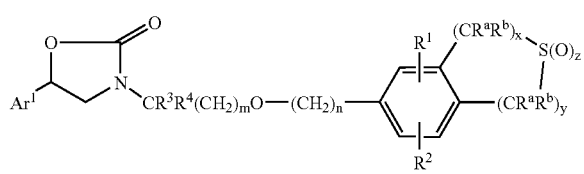

or a salt or solvate thereof, wherein $Ar^1$, $R^1$, $R^2$, $R^3$, $R^4$, m, n, x, y and z are as defined for the compound of formula (II) or (III).

The conversion of a compound of formula (VIII) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

A compound of formula (VIII) may be prepared by reacting a compound of formula (IX):

with a compound of formula (V) as hereinbefore defined.

The coupling of a compound of formula (IX) with a compound of formula (V) may be effected in the presence of a base, such as a metal hydride, for example sodium hydride, or an inorganic base such as cesium carbonate, in an aprotic solvent, for example N,N-dimethylformamide or tetrahydrofuran.

Compounds of formula (IX) may be prepared for example as described in WO 02/066422:

In a further process (c) a compound of formula (I), may be prepared by reacting a compound of formula (X):

wherein $Ar^1$ and $P^1$ are as hereinbefore defined and L is a leaving group as hereinbefore defined, with an amine of formula (XI):

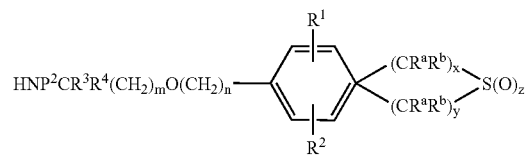

wherein $R^a$, $R^b$, $R^1$, $R^2$, $R^3$, $R^4$, $P^2$, m, n, x, y and z are as defined for formula (II); followed by removal of any protecting groups present by conventional methods as described above for the deprotection of compounds of formula (II).

The reaction may be effected using conventional conditions for such displacement reactions.

Compounds of formula (X) may be prepared by methods known in the art.

Compounds of formula (XI) may be prepared by reacting a compound of formula (V) with an amine $P^2NH_2$.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The enantiomeric compounds of the invention may be obtained (i) by separation of the components of the corresponding racemic mixture, for example, by means of a chiral chromatography column, enzymic resolution methods, or preparing and separating suitable diastereoisomers, (ii) by direct synthesis from the appropriate chiral intermediates by the methods described above, or (iii) by enantioselective oxidation of the sulphur atom.

Optional conversions of a compound of formula (I) to a corresponding salt may conveniently be effected by reaction with the appropriate acid or base. Optional conversion of a compound of formula (I) to a corresponding solvate or physiologically functional derivative may be effected by methods known to those skilled in the art.

In a preferred embodiment, in any of the processes described above, $Ar^1$ represents a group (ia):

For a better understanding of the invention, the following Examples are given by way of illustration.

SYNTHETIC EXAMPLES

Throughout the examples, the following abbreviations are used:
LC: Liquid Chromatography
LCMS: Liquid Chromatography Mass Spectrometry.
RT: retention time
THF: tetrahydofuran
DMF: N,N-dimethylformamide
MeCN: acetonitrile
$PPh_3$: triphenylphosphine AcOH: glacial acetic acid
EtOAc: ethyl acetate
PE: petroleum ether
EtOH: ethanol
BBN: 9-borabicyclo[3.3.1]nonane
bp: boiling point
ca: circa
h: hour(s)
min: minute(s)
All temperatures are given in degrees centigrade.
Silica gel refers to Merck silica gel 60 Art number 7734.
Flash silica gel refers to Merck silica gel 60 Art number 9385.
Biotage refers to prepacked silica gel cartridges containing KP-Sil run on flash 12i chromatography module.
SPE Bond Elut are prepacked cartridges used in parallel purifications, normally under vacuum. These are commercially available from Varian.
NMR experiments at 400 MHz (unless specified otherwise).
LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 100% B, 5.3-5.5 min 0% B at a flow rate of 3 ml/min. The mass spectra were recorded on a Fisons VG Platform spectrometer using electrospray positive and negative mode (ES+ve and ES−ve).
Preparative mass directed HPLC was conducted on a Waters FractionLynx system comprising of a Waters 600 pump with extended pump heads, Waters 2700 autosampler, Waters 996 diode array and Gilson 202 fraction collector on a 10 cm×2.54 cm ID ABZ+column, eluting with 0.1% formic acid in water (solvent A) and 0.1% formic acid in acetonitrile (solvent B), using the following elution gradient: 0.0-1.0 min 15% B, 1.0-10.0 min 55% B, 10.0-14.5 min 99% B, 14.5-14.9 min 99% B, 14.9-15.0 min 15% B at a flow rate of 20 ml/min and detecting at 200-320 nm at room temperature. Mass spectra were recorded on Micromass ZMD mass spectrometer using electrospray positive and negative mode, alternate scans. The software used was MassLynx 3.5 with OpenLynx and FractionLynx options.

Example 1

4-[(1R)-2-({6-[4-(1,1-Dioxido-2,3-dihydro-1-benzothien-6-yl)butoxy]hexyl}amino)-1-hydroxyethyl]-2-(hydroxymethyl)phenol acetate i) 2,3-Dihydro-1-benzothiophen-6-amine 1,1-dioxide A solution of 6-nitro-1-benzothiophene 1,1-dioxide (1.04 g) in acetic acid (50 ml) and ethyl acetate (50 ml) was hydrogenated over (10% palladium on carbon (130 mg, 50% wet). The catalyst was removed by filtration and washed with ethyl acetate. The filtrate and washings were evaporated under reduced pressure to give the title compound (1.1 g). LCMS RT=1.50 min ii) 6-Iodo-2,3-dihydro-1-benzothiophene 1,1-dioxide A mixture of 2,3-dihydro-1-benzothiophen-6-amine 1,1-dioxide (1.1 g) 2M hydrochloric acid (14 ml) was cooled in an ice-bath. Sodium nitrite (355 mg) in water (5 ml) was added dropwise and the mixture was stirred for 15 min before aqueous potassium iodide (830 mg) was added. The mixture was stirred overnight, before it was heated to 65° C. for 0.5 h. The mixture was cooled to 20° C. and extracted into ethyl acetate. The organic solution was washed with aqueous sodium metabisulfite solution, brine, dried and purified on two SPE silica cartridges (10 g) eluting with dichloromethane, diethyl ether and ethyl acetate. The dichloromethane fractions were combined and evaporated to give the title compound (550 mg) LCMS RT=2.65 min.

iii) 6-{3-[(6-Bromohexyl)oxy]propyl}-2,3-dihydro-1-benzothiophene 1,1-dioxide and 6-{3-[(6-iodohexyl)oxy]propyl}-2,3-dihydro-1-benzothiophene 1,1-dioxide A solution of 6-bromohexyl but-3-enyl ether (282 mg) in tetrahydrofuran (1 ml) was treated with a solution of 9-BBN in THF (0.5 M, 2.88 ml) at 20° C. under nitrogen. The mixture was stirred for 2 h and then tri-potassium phosphate (530 mg) in water (0.75 ml) was added, followed by 6-iodo-2,3-dihydro-1-benzothiophene 1,1-dioxide (550 mg) in THF (3 ml), palladium diacetate (0.27 mg) and triphenylphosphine (0.62 mg) and the mixture was heated under nitrogen to 65° C. for 2 h. The reaction mixture was concentrated and then applied to a silica SPE cartridge (10 g) eluting with dichloromethane-petrol (1:1), dichloromethane, diethyl ether to give the title compounds (370 mg) LCMS RT=3.59 min, ES+ve 420 and 422 $(M+NH_4)^+$ (bromide) and RT=3.70 min, ES+ve 486 $(M+NH_4)+$(iodide).

iv) 4[(1R)-2-({6-[4-(1,1-Dioxido-2,3-dihydro-1-benzothien-6-yl)butoxy]hexyl}amino)-1-hydroxyethyl]-2-(hydroxymethyl)phenol acetate A mixture of (1R)-2-amino-1-(2,2-dimethyl-4H-1,3-benzodioxin-6-yl)ethanol (112 mg) and 6-{3-[(6-bromohexyl)oxy]propyl}-2,3-dihydro-1-benzothiophene 1,1-dioxide and 6-{3-[(6-iodohexyl)oxy]propyl}-2,3-dihydro-1-benzothiophene 1,1-dioxide (370 mg) in dimethylformamide (1 ml) was allowed to stand at room temperature overnight. The solution was concentrated under reduced pressure and the residue was dissolved in ethanol and applied to an SCX-2 cartridge (10 g) eluting with ethanol and then with 10% aqueous ammonia in ethanol. The ammoniacal fractions were concentrated and the residue was dissolved in acetic acid (4 ml) and water (2 ml) and heated to 65° C. for 15 min. The solvents were removed under reduced pressure and the residue was purified on silica SPE cartridge (10 g) eluting with a gradient of 0-15% [10% ammonia in ethanol]-dichloromethane over 17 min. Appropriate fractions were combined and evaporated under reduced pressure. The residue was dissolved in acetic acid and then evaporated to dryness to give the title compound (59 mg) LCMS RT=2.32 min, ES+ve 506 $(M+H)^+$.

Example 2

4-[(1R)-2-({6-[4-(1,1-Dioxido-3,4-dihydro-2H-thiochromen-7-yl)butoxy]hexyl}amino)-1-hydroxyethyl]-2-(hydroxymethyl)phenol formate i) Ethyl 3-[(3-bromophenyl)thio]propanoate A mixture of 1-bromo-3-iodobenzene (3 g) and 1,1'-bis(diphenylphosphino)ferrocene (90 mg) in dimethylformamide (10 ml) and triethylamine (2 ml) was treated with tris(dibenzylideneacetone)dipalladium (175 mg) at 20° C. under nitrogen. After 10 min ethyl 3-mercaptopropionate (1.14 ml) was added and the mixture was heated to 60° C. for 1.5 h. The mixture was diluted with ethyl acetate and washed with 2M hydrochloric acid, brine and dried (MgSO$_4$). The filtrate was concentrated and chromatographed on a biotage cartridge (40 g) eluting with dichloromethane-cyclohexane (1:3) to give the title compound (1.58 g) LCMS RT=3.50 min ii) 3-[(3-Bromophenyl)thio]propanoic acid A solution of ethyl 3-[(3-bromophenyl)thio]propanoate (1.15 g) in ethanol (5 ml) was treated with aqueous sodium hydroxide solution (2M, 5 ml) and the mixture was stirred at 20° C. for 15 h. The mixture was acidified with hydrochloric acid and the solution was extracted with ethyl acetate. The organic solution was washed with hydrochloric acid, brine, dried (MgSO$_4$), and evaporated to give the title compound (390 mg) LCMS RT=3.19 min iii) 7-Bromo-2,3-dihydro-4H-thiochromen-4-one A mixture of 3[(3-bromophenyl)thio]propanoic acid (390 mg) and concentrated sulfuric acid (1.6 ml) was allowed to stand at 20° C. for 4 days. Water was added and the mixture was extracted with ethyl acetate. The organic solution was washed with sodium bicarbonate solution, brine, dried (MgSO$_4$) and evaporated. The residue was purified by chromatography on a silica SPE cartridge (10 g) eluting with cyclohexane, dichloromethane-cyclohexane (1:2, 1:1) and dichloromethane to give the title compound (116 mg) $^{13}$C NMR δ (CDCl$_3$) 193.5, 144.4, 131.0, 130.3, 130.0, 128.9, 128.8, 39.6, 27.1.

iv) 7-Bromothiochromane

A solution of 7-bromo-2,3-dihydro-4H-thiochromen-4-one (1 g) in trifluoroacetic acid (12 ml) was treated with triethylsilane (1.48 ml) and the mixture was stirred at reflux for 4 h. Water was added and the mixture extracted with ethyl acetate. The organic solution was washed with brine, dried (Na$_2$SO$_4$) and evaporated. The residue was purified by chromatography on a Biotage cartridge (40 g) eluting with petrol-diethyl ether (10:1) to give the title compound (946 mg). LCMS RT=3.71 min v) 7-Bromothiochromane 1,1-dioxide 3-Chloroperoxybenzoic acid (2.8 g) was added to a cooled solution of 7-bromothiochromane (946 mg) in dry dichloromethane (50 ml). The mixture was stirred at room temperature for 1 h and then washed with 2N sodium sulphite solution. The organic solution was filtered through neutral alumina and concentrated to give the title compound (200 mg) LCMS RT=2.71 min vi) 7-{4-[(6-Bromohexyl)oxy]butyl}thiochromane 1,1-dioxide To a solution of 4-[(6-bromohexyl)oxy]but-1-ene (180 mg) in tetrahydrofuran (0.6 ml) was added a 0.5M solution of 9-borabicyclo[3.3.1]nonane in tetrahydrofuran (1.8 ml). The solution was stirred at room temperature, under nitrogen for 2 h. Tripotassium phosphate (324 mg) in water (0.46 ml) was added, followed by 7-bromothiochromane 1,1-dioxide (200 mg), palladium (II) acetate (2 mg) and triphenylphosphine (4 mg). The resultant mixture was heated at 60° C. for 17 h. Water was added and the organic layer washed with brine, dried (Na$_2$SO$_4$) and evaporated. The residue was purified by chromatography on a Biotage cartridge (40 g) eluting with cyclohexane-ethyl acetate (1:1) to give the title compound (121 mg) LCMS RT=3.66 min vii) (1R)-1-(2,2-Dimethyl4H-1,3-benzodioxin-6-yl)-2-({6-[4-(1,1-dioxido-3,4-dihydro-2H-thiochromen-7-yl)butoxy]hexyl}amino)ethanol To a solution of (1R)-2-amino-1-(2,2-dimethyl4H-1,3-benzodioxin-6-yl)ethanol (128 mg) in dry tetrahydrofuran (6 ml) and dimethylformamide (2 ml) was added diisopropylethylamine (0.066 ml) and 7-{4[(6-bromohexyl)oxy] butyl}thiochromane 1,1-dioxide (120 mg). The reaction mixture was heated at 50° C. for 17 h. The mixture was then concentrated in vacuo and the residue was purified by chromatography on a Biotage cartridge (8 g) eluting with dichloromethane-ethanol-aqueous ammonia solution (100: 8:1) to give the title compound (134 mg). LCMS RT=2.74 min viii) 4-[(1R)-2-({6-[4-(1,1-Dioxido-3,4-dihydro-2H-thiochromen-7-yl)butoxy]hexyl}amino)-1-hydroxyethyl]-2-(hydroxymethyl)phenol formate A solution of (1R)-1-(2,2-dimethyl4H-1,3-benzodioxin-6-yl)-2-({6-[4(1,1-dioxido-3,4-dihydro-2H-thiochromen-7-yl)butoxy]hexyl}amino)ethanol (134 mg) in glacial acetic acid (10 ml) and water (5 ml) was heated at 80° C. for 40 min. The mixture was concentrated in vacuo and the residue purified by mass directed autoprep to give the title compound (79 mg). LCMS RT=2.46 min, ES+ve 520 (MH)$^+$.

Biological Activity

In Vitro Measurements of Compound Potency and Intrinsic Activity at the Human Beta 1, 2 and 3 Receptor.

Method

Potency of compounds of the invention at the human beta 2, 1 and 3 receptors was determined using Chinese hamster ovary cells co-expressing the human receptor with a reporter gene. Studies were performed using either whole cells or membranes derived from those cells.

The three beta-receptors are coupled via the Gs G-protein to cause a stimulation of adenylate cyclase resulting in increased levels of cAMP in the cell. For direct cAMP measurements either membranes or frozen cells have been used with either the HitHunter enzyme fragment complementation kit (DiscoveRx) or the FP$^2$ fluorescence polarisation kit (Perkin Elmer) to quantify the levels of CAMP present. These assays provide a measure of agonist potency and intrinsic activity of the compounds at the various receptors.

In this assay the potency of compounds at the human beta-2 receptor is expressed as a pEC$_{50}$ value. Compounds of Examples 1 and 2 had a pEC$_{50}$ of >6.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

What is claimed is:

1. A compound of formula (I)

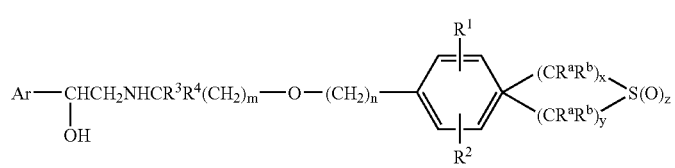

or a salt, solvate, or physiologically functional derivative thereof, wherein:
m is an integer of from 2 to 8;
n is an integer of from 3 to 11;
with the proviso that m+n is 5 to 19;
x is zero and y is an integer of 2 or 3 or
y is zero and x is an integer of 2 or 3;
z is zero or an integer of 1 or 2;
$R^a$ and $R^b$ are independently selected from hydrogen and $C_{1-4}$alkyl;
$R^1$ and $R^2$ are independently selected from hydrogen, $C_{1-6}$alkyl, $C_{1-6}$alkoxy, halo, phenyl, and $C_{1-6}$haloalkyl;
$R^3$ and $R^4$ are independently selected from hydrogen and $C_{1-4}$alkyl with the proviso that the total number of carbon atoms in $R^3$ and $R^4$ is not more than 4;
Ar is a group selected from

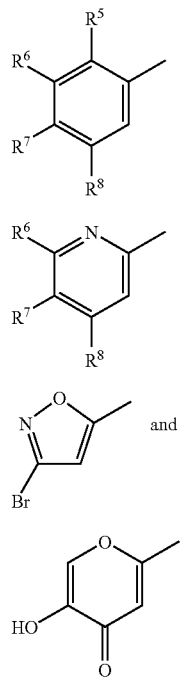

wherein $R^6$ represents hydrogen, halogen, $-(CH_2)_qOR^9$, $-NR^9C(O)R^{10}$, $-NR^9SO_2R^{10}$, $-SO_2NR^9R^{10}$, $-NR^9R^{10}$, $-OC(O)R^{11}$ or $-OC(O)NR^9R^{10}$,
and $R^5$ represents hydrogen, halogen or $C_{1-4}$alkyl;
or $R^6$ represents $-NHR^{12}$ and $R^5$ and $-NHR^{12}$ together form a 5- or 6-membered heterocyclic ring;
$R^7$ represents hydrogen, halogen, $-OR^9$ or $-NR^9R^{10}$;

$R^8$ represents hydrogen, halogen, halo$C_{1-4}$ alkyl, $-OR^9$, $-NR^9R^{10}$, $-OC(O)R^{11}$ or $-OC(O)NR^9R^{10}$;

$R^9$ and $R^{10}$ independently represent hydrogen or $C_{1-4}$ alkyl or $R^9$ and $R^{10}$ together with the nitrogen atom to which they are attached form a 5-, 6- or 7-membered nitrogen-containing ring,
$R^{11}$ represents an aryl (eg phenyl or naphthyl) group which may be unsubstituted or substituted by one or more substituents selected from halogen, $C_{1-4}$ alkyl, hydroxy, $C_{1-4}$ alkoxy or halo $C_{1-4}$ alkyl; and
q is zero or an integer from 1 to 4.

2. A compound according to claim 1 wherein $R^3$ and $R^4$ are independently selected from hydrogen and methyl.

3. A compound according to claim 1 wherein $R^1$ and $R^2$ each represent hydrogen.

4. A compound according to claim 1 wherein the integer m is 4, 5 or 6 and n is 3, 4, 5 or 6.

5. A compound according to claim 1 wherein the group Ar is selected from groups (a) and (b)

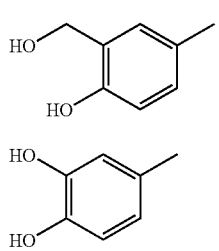

6. A compound according to claim 5 wherein groups (a) and (b) are selected from the group consisting of (i) to (xxi):

-continued
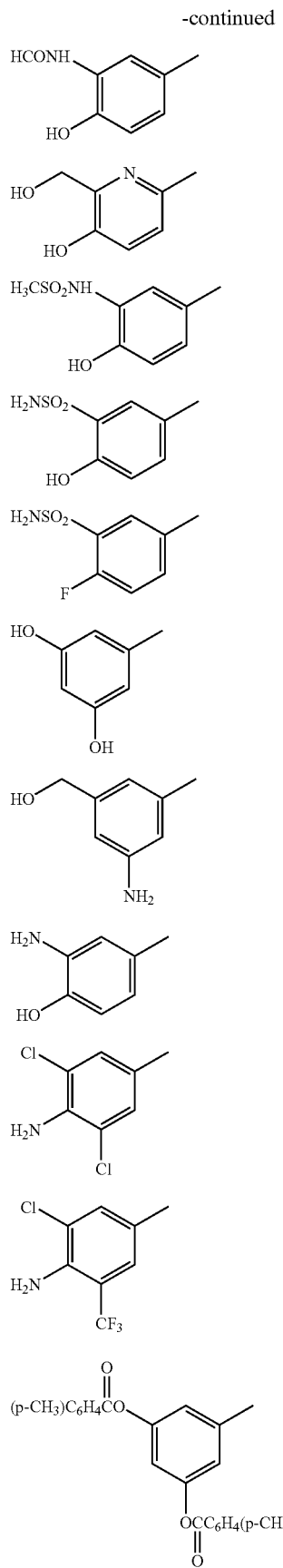
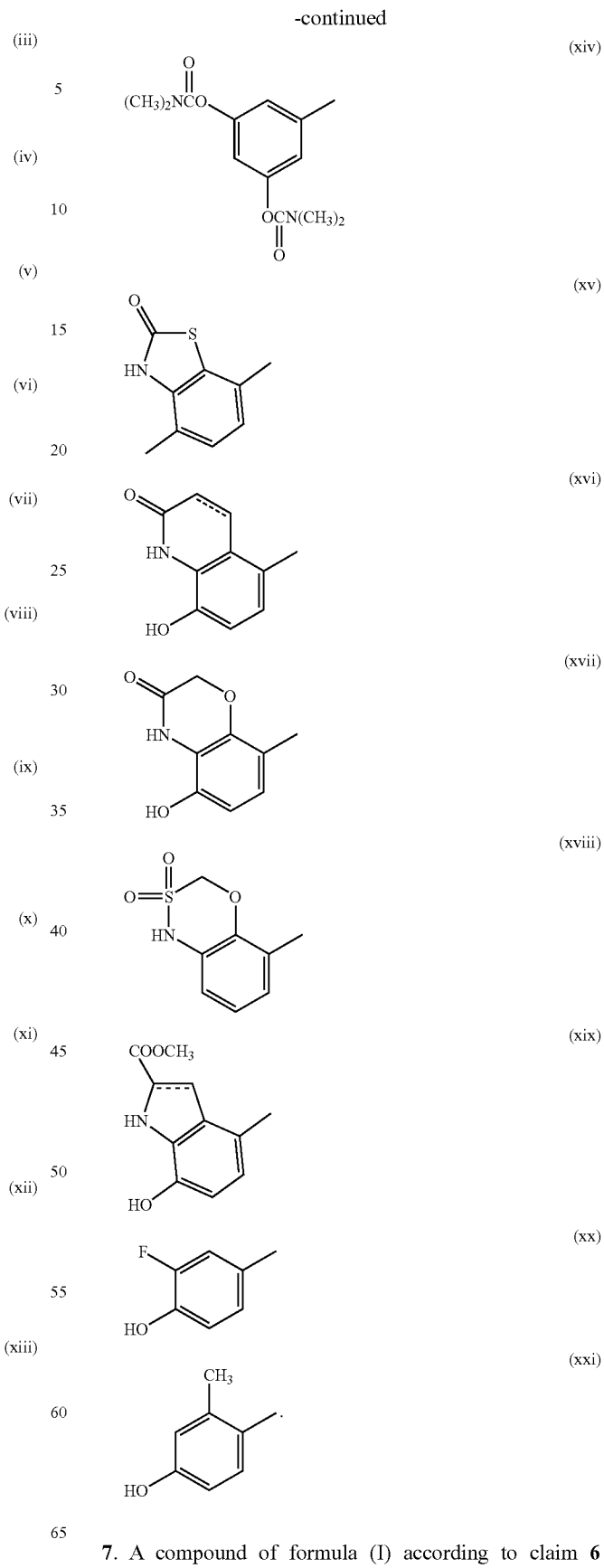
7. A compound of formula (I) according to claim 6 wherein Ar represents group (i)

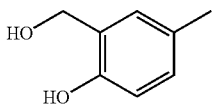

(i)

8. A compound of formula (I) according to claim 1 wherein z represents 2.

9. A compound of formula (I) according to claim 1 which is selected from the group consisting of:
4-[(1R)-2-({6-[4-(1,1-Dioxido-2,3-dihydro-1-benzothien-6-yl)butoxy]hexyl}amino)-1-hydroxyethyl]-2-(hydroxymethyl)phenol;
4-[(1r)-2-({6-[4-(1,1-dioxido-3,4-dihydro-2h-thiochromen-7-yl)butoxy]hexyl}amino)-1-hydroxyethyl]-2-(hydroxymethyl)phenol;
salts thereof, solvates thereof and physiologically functional derivatives thereof.

10. A method for the prophylaxis or treatment of a clinical condition in a mammal for which a selective β$_2$-adrenoreceptor agonist is indicated, which comprises administating a therapeutically effective amount of a compound of formula (I), according to claim 1, or a pharmaceutically acceptable salt, solvate, or physiologically functional derivative thereof.

11. A pharmaceutical formulation comprising a compound of formula (I), according to claim 1, or a pharmaceutically acceptable salt, solvate, or physiologically functional derivative thereof, and a pharmaceutically acceptable carrier or excipient, and optionally one or more other therapeutic ingredients.

12. A process for the preparation of a compound of formula (I), according to claim 1, or a salt, solvate, or physiologically functional derivative thereof, which comprises
deprotecting a protected intermediate of formula (II):

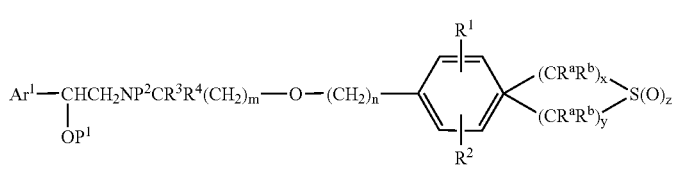

(II)

or a salt or solvate thereof, wherein $R^a$, $R^b$, $R^1$, $R^2$, $R^3$, $R^4$, m, n; x, y and z are as defined for the compound of formula (I) or (Ia), $Ar^1$ represents an optionally protected form of Ar; and $P^1$ and $P^2$ are each independently either hydrogen or a protecting group, such that the compound of formula (II) contains at least one protecting group
wherein said deprotecting step is optionally followed by one or more of the following steps in any order selected from the group consisting of:
(i) removing any protecting groups;
(ii) separating an enantiomer from a mixture of enantiomers;
(iii) converting one compound of formula (I) to a different compound of formula (I); and (iv) converting the product to a corresponding salt, solvate, or physiologically functional derivative thereof.

13. A process for the preparation of a compound of formula (I), according to claim 1, or a salt, solvate, or physiologically functional derivative thereof, which comprises reacting a compound of formula (IV):

(IV)

wherein $Ar^1$ represents an optionally protected form of Ar; and $P^1$ and $P^2$ each independently represent hydrogen or a protecting group, with a compound of formula (V):

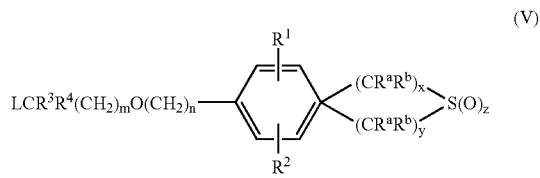

(V)

wherein L is a leaving group, and $R^a$, $R^b$, $R^1$, $R^2$, $R^3$, $R^4$, n, m, x, y and z are as defined for compounds of formula (I);
wherein said reacting step is optionally followed by one or more of the following steps in any order selected from the group consisting of:
(i) removing any protecting groups;
(ii) separating an enantiomer from a mixture of enantiomers;
(iii) converting one compound of formula (I) to a different compound of formula (I); and
(iv) converting the product to a corresponding salt, solvate, or physiologically functional derivative thereof.

14. A process for the preparation of a compound of formula (I), according to claim 1, or a salt, solvate, or physiologically functional derivative thereof, which comprises reacting a compound of formula (X):

(X)

wherein $Ar^1$ represents an optionally protected form of Ar; $P^1$ independently represents hydrogen or a protecting group and L is a leaving group, with an amine of formula (XI):

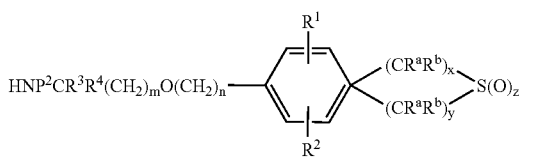

(XI)

wherein $R^a$, $R^b$, $R^1$, $R^2$, $R^3$, $R^4$, m, n, x, y and z are as defined; and $P^2$ represents hydrogen or a protecting group;
wherein said reacting step is optionally followed by one or more of the following steps in any order selected from the group consisting of:
(i) removing any protecting groups;
(ii) separating an enantiomer from a mixture of enantiomers;
(iii) converting one compound of formula (I) to a different compound of formula (I); and
(iv) converting the product to a corresponding salt, solvate, or physiologically functional derivative thereof.

15. The method according to claim 10, wherein the mammal is a human.

16. The process according to claim 13, wherein L is a halo or sulfonate leaving group.

17. The process according to claim 16, wherein L is selected from the group consisting of an alkylsulfonate, an aryl sulfonate, and a haloalkylsulfonate.

18. The process according to claim 14, wherein L is a halo or sulfonate leaving group.

19. The process according to claim 18, wherein L is selected from the group consisting of an alkylsulfonate, an aryl sulfonate, and a haloalkylsulfonate.

* * * * *